(12) United States Patent
Jeanne

(10) Patent No.: US 9,532,745 B2
(45) Date of Patent: Jan. 3, 2017

(54) BREATHING GUIDANCE APPARATUS FOR DELIVERY ROOMS

(71) Applicant: Koninklijke Philips N.V., Eindhoven (NL)

(72) Inventor: Vincent Jeanne, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 94 days.

(21) Appl. No.: 14/343,494

(22) PCT Filed: Sep. 20, 2012

(86) PCT No.: PCT/IB2012/054980
§ 371 (c)(1),
(2) Date: Mar. 7, 2014

(87) PCT Pub. No.: WO2013/046094
PCT Pub. Date: Apr. 4, 2013

(65) Prior Publication Data
US 2014/0249383 A1 Sep. 4, 2014

Related U.S. Application Data

(60) Provisional application No. 61/539,097, filed on Sep. 26, 2011.

(51) Int. Cl.
*A61B 5/00* (2006.01)
*A61M 21/02* (2006.01)
(Continued)

(52) U.S. Cl.
CPC .............. *A61B 5/486* (2013.01); *A61B 5/0077* (2013.01); *A61B 5/0205* (2013.01); *A61B 5/4356* (2013.01); *A61B 5/7278* (2013.01); *A61B 5/7455* (2013.01); *A61M 21/02* (2013.01); *A61B 5/0816* (2013.01); *A61M 2021/005* (2013.01);
(Continued)

(58) Field of Classification Search
CPC ... A61B 5/0002; A61B 5/0205; A61B 5/1113; A61B 5/1128; A61B 5/743; A61B 5/7435; A61B 5/7475; A61B 5/486; A61B 5/0013; A61B 5/4356; A61B 5/742; G06F 19/3418; G06F 19/345; G06F 19/3406; G06F 19/321; Y10S 128/92
See application file for complete search history.

(56) References Cited

U.S. PATENT DOCUMENTS 3,991,304 A 11/1976 Hillsman
4,711,585 A 12/1987 Fresquez et al.
(Continued)

FOREIGN PATENT DOCUMENTS

JP 2007532169 A 11/2007
JP 2010214134 A 9/2010
(Continued)

*Primary Examiner* — Deborah Malamud

(57) ABSTRACT

A system to prompt a subject to consciously alter one or more physiological parameters during childbirth-related contractions includes an imaging subsystem, a contraction sensor, and various computer program modules. The computer program module are configured to determine a physiological parameter, contraction information, a target action rate, and cues based thereon. The physiological parameter may include a breathing rate. The target action rate may include a target breathing rate. The cues may include breathing cues.

15 Claims, 3 Drawing Sheets

(51) Int. Cl.
    *A61B 5/0205*     (2006.01)
    *A63B 23/18*     (2006.01)
    *A61M 21/00*     (2006.01)
    *A61B 5/08*     (2006.01)

(52) U.S. Cl.
    CPC ........... *A61M 2021/0016* (2013.01); *A61M 2021/0022* (2013.01); *A61M 2021/0027* (2013.01); *A61M 2205/581* (2013.01); *A61M 2205/582* (2013.01); *A61M 2205/588* (2013.01); *A61M 2230/005* (2013.01); *A61M 2230/06* (2013.01); *A61M 2230/205* (2013.01); *A61M 2230/62* (2013.01); *A61M 2230/63* (2013.01); *A63B 23/185* (2013.01)

(56) References Cited

U.S. PATENT DOCUMENTS

| | | |
|---|---|---|
| 5,704,367 A | 1/1998 | Ishikawa et al. |
| 6,212,135 B1 | 4/2001 | Schreiber |
| 2008/0027357 A1 | 1/2008 | Owen |
| 2008/0294022 A1 | 11/2008 | Sharf et al. |

FOREIGN PATENT DOCUMENTS

| | | |
|---|---|---|
| RU | 2134542 C1 | 8/1999 |
| WO | 2005096707 A2 | 10/2005 |
| WO | 2012140531 A1 | 10/2012 |

BREATHING GUIDANCE APPARATUS FOR DELIVERY ROOMS

This present disclosure pertains to providing cues to a subject, and in particular, in accordance with a breathing regime associated with labor contractions.

It is known that breathing regimes associated with labor contractions (e.g., Lamaze breathing) may be used by expectant mothers during childbirth to reduce pain and/or improve relaxation and/or comfort. These breathing regimes are typically associated with labor contractions. For example, at the onset of a labor contraction, the breathing regime may temporarily shift from a slow breathing rate to a more rapid breathing rate. During labor and/or in-between contractions, an expectant mother may need assistance to help conform her breathing rate and/or breathing pattern to an appropriate breathing regime.

Accordingly, an aspect of one or more embodiments of the present disclosure to provide a system configured to prompt a subject to consciously alter one or more physiological parameters during childbirth-related contractions. The system comprises an imaging subsystem configured to generate image information related to visual images of the subject during childbirth-related contractions; a contraction sensor configured to generate contraction signals conveying information related to contractions of the subject; a user interface; a parameter determination module configured to determine a physiological parameter of the subject based on the generated image information; a contraction detection module configured to determine contraction information based on the generated contraction signals from the contraction sensor; a target action module configured to determine cues for the subject based on the physiological parameter and the contraction information, wherein the cues prompt the subject to modulate one or more physiological parameters in coordination with the contractions of the subject; and a user interface module configured to communicate the cues to the subject via the user interface.

It is yet another aspect of one or more embodiments of the present disclosure to provide a method for prompting a subject to consciously alter one or more physiological parameters during childbirth-related contractions. The method comprises capturing image information related to visual images of the subject during childbirth-related contractions; determining a physiological parameter of the subject based on the captured image information; generating contraction signals conveying information related to contractions of the subject; determining contraction information based on the generated contraction signals; determining cues for the subject based on the physiological parameter and the contraction information, wherein the cues prompt the subject to modulate one or more physiological parameters in coordination with the contractions of the subject; and communicating the cues to the subject.

It is yet another aspect of one or more embodiments of the present disclosure to provide a system configured for prompting a subject to consciously alter one or more physiological parameters during childbirth-related contractions. The system comprises means for capturing image information related to visual images of the subject during childbirth-related contractions; means for determining a physiological parameter of the subject based on the captured image information; means for generating contraction signals conveying information related to contractions of the subject; means for determining contraction information based on the generated contraction signals; means for determining cues for the subject based on the physiological parameter and the contraction information, wherein the cues prompt the subject to modulate one or more physiological parameters in coordination with the contractions of the subject; and means for communicating the cues to the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 1:
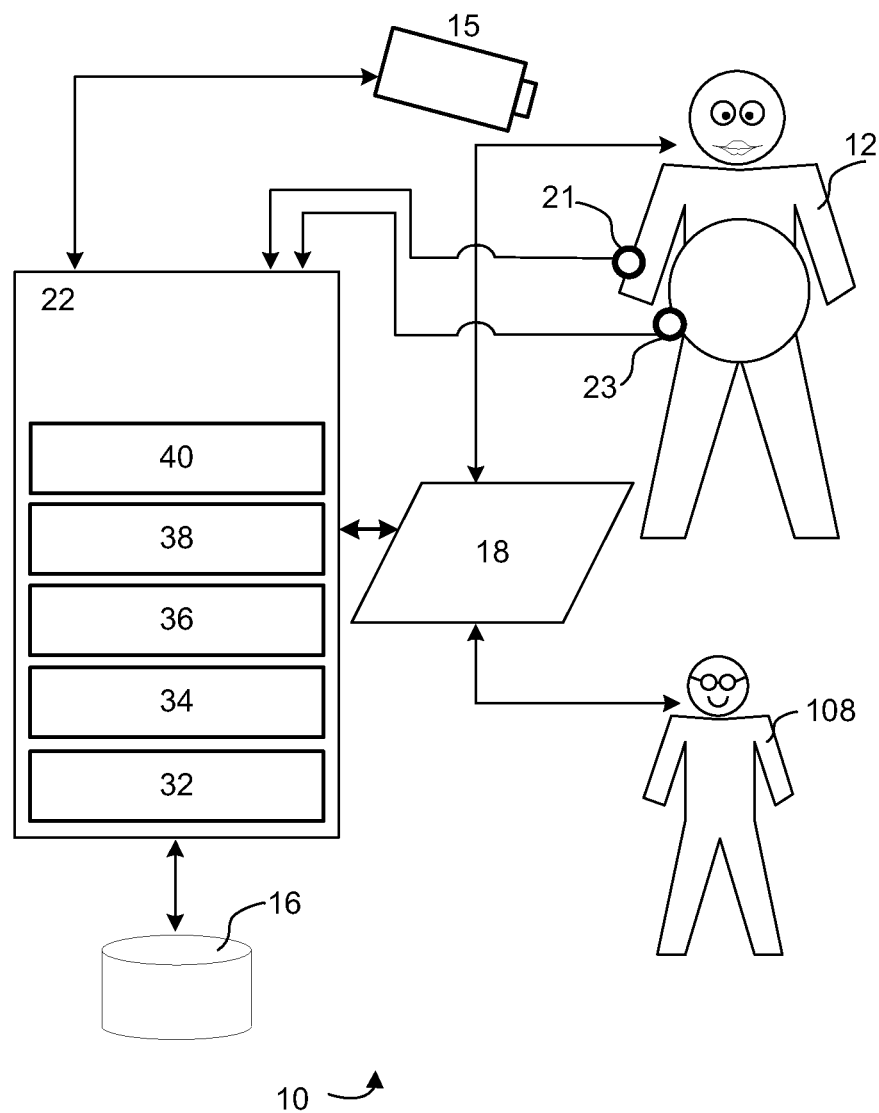
FIG. 1 illustrates a system configured to prompt a subject to consciously alter one or more physiological parameters during childbirth-related contractions, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to prompt a subject 12 (i.e. an expectant mother) to consciously alter one or more physiological parameters during childbirth-related contractions, in accordance with one or more embodiments. System 10 may include one or more of an imaging subsystem 15, electronic storage 16, a user interface 18, a contraction sensor 23, one or more physiological sensors 21, a processor 22, and/or other components.

Imaging subsystem 15 of system 10 in FIG. 1 may be configured to capture image information related to visual images of subject 12 during childbirth-related contractions. Imaging subsystem 15 may comprise one or more of an imaging sensor (not shown), one or more optical elements (e.g., a lens, a mirror, a filter, and/or other elements), a power supply, and/or other components. Imaging subsystem 15 is configured to output image information that is processed to derive still and/or video images. Imaging subsystem 15 may operate without making physical contact with subject 12, i.e. in a contact-free manner. The captured image information may be used to determine one or more physiological parameters of subject 12. For example, the one or more physiological parameters may include one or more breathing parameters (e.g., breathing rate, tidal volume, and/or other parameters), one or more parameters of the contractions (e.g., frequency, duration, intensity, and/or other parameters), one or more cardiovascular parameters (e.g., pulse, pulse shape, blood pressure, and/or other parameters), and/or other physiological parameters of subject 12.

Contraction sensor 23 of system 10 in FIG. 1 may be configured to generate contraction signals conveying information related to contractions of subject 12. From such information, one or more parameters of the contractions may be derived. Such parameters may include, without limitation, frequency, duration, intensity, severity, onset, peak, end, and/or other parameters. As was mentioned above, in some embodiments, functionality attributed herein to contraction sensor 23 may be provided by imaging subsystem 15. In such embodiments, contraction sensor 23 may operate without making physical contact with subject 12, i.e. in a contact-free manner In some embodiments, the contraction signals may convey information used to derive an intensity and/or severity level of the contraction, e.g. using threshold levels, percentages, and/or other indicators of severity or intensity of a contraction.

Contraction sensor 23 of system 10 may be part of a contraction monitor. Typically, a contraction monitor is configured to monitor and communicate one or more of the frequency, magnitude, and pattern of contractions during labor. For example, the contraction monitor may monitor and communicate the beginning/onset of a contraction and the end of the contraction such that the length and pattern of contractions may be calculated. The contraction monitor may include a fetal monitor that monitors the fetus's heart rate. The contraction monitor may be any type of sensor that monitors the labor contractions and outputs signals associated with the labor contractions. Furthermore, the contraction monitor may be external or internal and may communicate output signals via signal cables or wirelessly (e.g., IrDA, RFID (Radio Frequency Identification), Wireless USB). For example, the contraction monitor may include pressure transducers or strain gauges held against subject 12's abdomen by an elastic belt placed around subject 12's waist. Contraction monitor may comprise internal catheters inserted into the uterus to measure changes in the amniotic fluid pressure in the amniotic sac. Alternatively or additionally, the contraction monitor may include a fiber optic strain sensor that generates signals in response to labor contractions and wirelessly communicates the output signals via a transceiver. Various attachment mechanisms, if needed, may be used to attach a contraction monitor to subject 12, such as, for example, an elastic band, a belt, and/or adhesive materials. Any function or feature attributed herein to a contraction monitor may be incorporated and/or included in system 10 in general, and, in particular, to contraction sensor 23 of system 10.

Electronic storage 16 of system 10 in FIG. 1 may comprise electronic storage media that electronically stores information. The electronically storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., user interface 18, processor 22, etc.).

User interface 18 is configured to provide an interface between system 10, subject 12, and/or a user 108 (such as, e.g., a healthcare provider or caregiver) through which information may be provided to and received from system 10, subject 12, and/or user 108. This enables data, results, and/or instructions and any other communicable items, collectively referred to as "information," to be communicated between, e.g., subject 12 and one or more of electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, haptic technology, tactile feedback systems, and/or other interface devices. Information from user interface 18 may be provided to the user by auditory means, visual means, tactile means, and/or via some other sensory feedback. In one embodiment, user interface 18 includes a plurality of separate interfaces. In one embodiment, user interface 18 includes at least one interface that is provided integrally with system 10.

It is to be understood that other communication techniques, either hard-wired or wireless, are also contemplated to be used as user interface 18. For example, the present disclosure contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated to be used as user interface 18.

One or more physiological sensors 21 may be configured to sense physiological parameters of, e.g., subject 12. For example, sensors 21 may include a pulse oximeter configured to monitor the oxygen saturation of a patient's blood. Sensors 21 may also include a cardiac monitor to monitor, for example, subject 12's cardiac rhythm and/or heart rate variability. Some or all of these physiological parameters may be based on captured image information, from, e.g., imaging subsystem 15, related to visual images of subject 12. It should be appreciated that the sensors 21 may also include other types of sensors and/or any combination and number thereof.

One or more processors 22 are configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device, or processor 22 may represent processing functionality of a plurality of devices operating in coordination.

As is shown in FIG. 1, processor 22 may be configured to execute one or more computer program modules. The one or more computer program modules may include one or more of a parameter determination module 32, a breathing detection module 34, a contraction detection module 36, a target action module 38, an interface module 40, and/or other modules. Processor 22 may be configured to execute modules 32, 34, 36, 38, and/or 40 by software; hardware; firmware; some combination of software, hardware, and/or firmware; and/or other mechanisms for configuring processing capabilities on processor 22.

It should be appreciated that although modules 32, 34, 36, 38, and 40 are illustrated in FIG. 1 as being co-located within a single processing unit, in implementations in which processor 22 includes multiple processing units, one or more of modules 32, 34, 36, 38, and/or 40 may be located remotely from the other modules. The description of the functionality provided by the different modules 32, 34, 36, 38, and/or 40 described below is for illustrative purposes, and is not intended to be limiting, as any of modules 32, 34, 36, 38, and/or 40 may provide more or less functionality than is described. For example, one or more of modules 32, 34, 36, 38, and/or 40 may be eliminated, and some or all of its functionality may be provided by other ones of modules 32, 34, 36, 38, and/or 40. As another example, processor 22 may be configured to execute one or more additional modules that may perform some or all of the functionality attributed below to one of modules 32, 34, 36, 38, and/or 40.

Parameter determination module 32 of system 10 in FIG. 1 may be configured to determine one or more physiological parameters (including, e.g., breathing parameters) of subject 12 from, e.g., the one or more output signals generated by imaging subsystem 15 and/or one or more physiological sensors 21. In some embodiments, the one or more determined physiological parameters may pertain to a physical action and/or movement performed by subject 12, such as, e.g., physical motion patterns that may improve relaxation. In some embodiments, the one or more determined parameters may include a breathing parameter that subject 12 is prompted to consciously alter through the provided breathing cues. In some embodiments, parameter determination module 32 may include (access to) a timer in order to determine, e.g., the duration of inhalation and exhalation and/or the breathing rate.

Breathing detection module 34 of system 10 in FIG. 1 is configured to determine a breathing rate of the subject. The determination of breathing detection module 34 may be based on the captured image information from imaging subsystem 15. In some embodiments, breathing detection module 34 may be configured to determine feedback related to the breathing rate of the subject during previous contractions. By using feedback, system 10 can adapt to subject 12, and adjust, e.g., the target breathing rate accordingly.

Contraction detection module 36 is configured to determine contraction information. The determination of contraction information may be based on the generated contraction signals from contraction sensor 23. Contraction information may include the onset, peak, intensity, severity, duration, end, and/or other parameters of a contraction. Contraction information may include information spanning multiple contractions, such as frequency, and/or trending information. Contraction information may be transmitted and/or shared with other computer program modules of system 10. In some embodiments, future contractions may be anticipated based on past contractions.

Target action module 38 is configured to determine and/or obtain a target action rate (which may include, e.g., a target breathing rate), which may be different than the current action and/or breathing rate of subject 12. The determination of the target action rate may be based on one or more of a current physiological parameter of subject 12, as determined, and the contraction information, and/or other information. For example, a target breathing rate may be determined based on physiological parameters, including any of the physiological parameters described herein in relation to imaging subsystem 15 and/or physiologic sensors 21. Target action module 38 is further configured to determine cues for the subject. The cues prompt the subject to modulate one or more physiological parameters in coordination with (and/or in-between) the contractions of the subject, based on the target action rate. In some embodiments, the target action rate includes a target breathing rate. In some embodiments, the cues include breathing cues. In some embodiments, a target breathing rate may be received from user 108 (e.g., a caregiver, subject 12, etc.). The user may, e.g., input the target breathing rate via user interface 18. Inputting the target breathing rate may include inputting a new target breathing rate, or adjusting a previously obtained target breathing rate.

The target action rate may be determined and/or adjusted based on any contraction information, physiological parameters (including, e.g., breathing parameters), cardiovascular parameters, and/or other information, including, e.g., the duration of the contractions and the stage of the contraction. The target action rate may be gradually adjusted to accommodate a smooth transition in the physiological parameter of subject 12, as determined. In response, the cues may be gradually adjusted correspondingly, to prompt subject 12 to change her current action rate and/or physiological parameter to approximate the target action rate. In some embodiments, target action module 38 may use information regarding the onset of a new contraction, as received from contraction detection module 36, and base the cues on this received information. In some embodiments, the target action rate may be based on (and/or correspond to) the intensity level of the contraction. In some embodiments, anticipated future contractions may form the basis for the target action rate. In some embodiments, operation of target action module 38 may be based, at least in part, of feedback received from breathing detection module 34 related to previous contractions.

Figure 2:
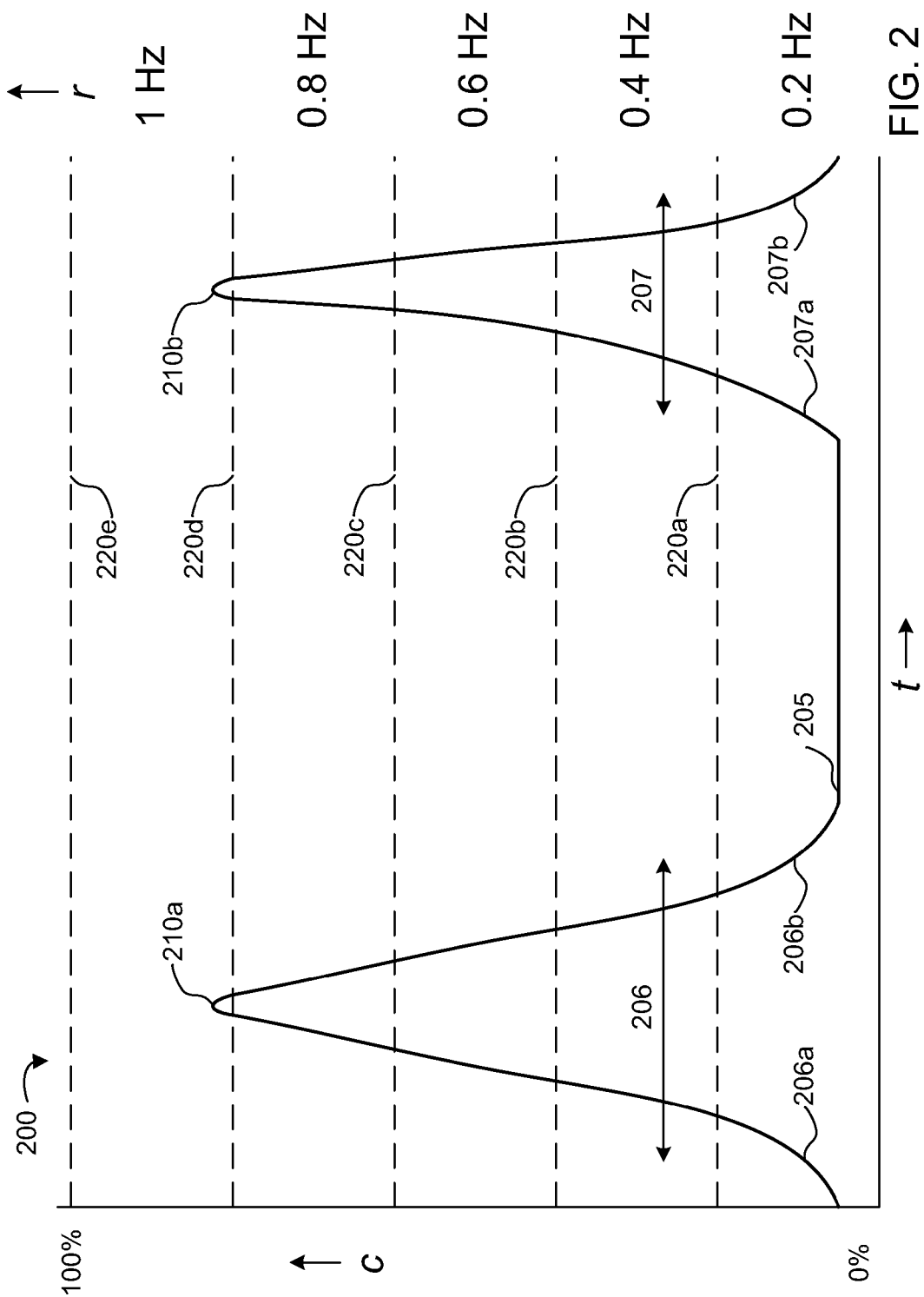
FIG. 2 illustrates a diagram that corresponds to the provision of breathing cues in accordance with one or more embodiments.

By way of illustration, FIG. 2 illustrates a diagram 200 that corresponds to the provision of breathing cues in accordance with one or more embodiments. Graph 205 shown the intensity and/or severity (labeled c on the Y-axis, in a percentage ranging from 0% to 100%) of contractions over time (labeled t on the X-axis). The contraction intensity may be determined based on contraction signals from contraction sensor 23. Duration 206 coincides with the first contraction in FIG. 2. Duration 207 coincides with the second contraction in FIG. 2. Onset 206a of the first contraction, as well as onset 207a of the second contraction, may be determined by the contraction intensity broaching a predetermined intensity threshold, such as, e.g., 5%, 8%, 10%, and/or another percentage. The end of a contraction, e.g. 206*b* and/or 207*b*, may be determined in a similar fashion. The peak of the first contraction is indicated by peak 210*a*. The peak of the second contraction is indicated by peak 210*b*. Duration 206 may be determined by comparing onset 206*a* with end of contraction 206*b*. Contraction detection module 36 may derive additional parameters from a measured contraction intensity graph such as graph 205. For example, such parameters may include the time from one peak to the next peak, a trend in peak levels or contraction frequency, and/or other derived parameters.

Diagram 200 includes intensity thresholds 220*a*-220*e* that may correspond to a target breathing rate r. As depicted in FIG. 2 as an example, and by no means intended to be limiting, the target breathing frequency during contraction intensity below 20% may be 0.2 Hz. The target breathing frequency during contraction intensity above 80% may be 1 Hz. Target action module 38 may adjust the target breathing rate, as depicted in FIG. 2, corresponding to a change in contraction intensity. Responsive to a change in target breathing rate, the breathing cues may be adjusted accordingly.

Interface module 40 of system 10 in FIG. 1 is configured to communicate the cues to the subject via user interface 18. In some cases, subject 12 may initially have difficulty determining what the provided cues are prompting subject 12 to do. The interface module 40 may be configured to dynamically (e.g., adjusted or updated based on the cues) provide information to subject 12 related to the meaning of the cues provided to subject 12. In one embodiment, interface module 40 controls user interface 18 to communicate the information related to the cues to subject 12. The information related to the cues may include, for the example of breathing cues, instructions to begin exhaling, to end exhaling, to begin inhaling, to end inhaling, to breathe faster, to breathe slower, to pause respiration, and/or to otherwise consciously alter one or more breathing parameters.

The information related to the cues may be provided to subject 12 by user interface 18 in the form of, e.g., auditory signals, visual signals, tactile signals, and/or other sensory signals. By way of non-limiting example, user interface 18 may include a radiation source capable of emitting light. The radiation source may include, for example, one or more of at least one LED, at least one light bulb, a display screen, and/or other sources. The interface module 40 may control the radiation source to emit light in a manner that conveys to subject 12 information related to the cues being provided to subject 12. For instance, the radiation source may emit light when the cues are prompting subject 12 to inhale, and may stop emitting light, or emit light of a different color, when the cues are prompting subject 12 to exhale. The intensity of the light emitted by the radiation source may convey to subject 12 the magnitude of the flow that the breathing cues are prompting subject 12 to generate during respiration.

A non-limiting example of the manner in which user interface 18 may communicate information about the cues to subject 12 is generating sounds that are audible to subject 12. The interface module 40 may control the element(s) to generate sounds that communicate to subject 12 the meaning of the cues being delivered to subject 12. For instance, interface module 40 may control the element(s) to emit a "beep" or other short burst of noise to indicate to subject 12 a transition between inhalation and exhalation, and/or that flow should be increased or decreased. The interface module 40 may control the element(s) to play word messages that indicate to subject 12 the meaning of the cues. The word messages may be prerecorded and stored within electronic storage 16.

As another non-limiting example of the manner in which user interface 18 may communicate information about the cues to subject 12, user interface 18 may include one or more devices that contact subject 12 and provide tactile feedback to subject 12. For instance, user interface 18 may include a cuff that is worn by subject 12 around an extremity such as an arm, a leg, a finger, and/or other extremities. The cuff may carry one or more sensors configured to detect a physiological parameter of subject 12, such as for example, pulse, pulse rate, respiratory effort, blood pressure, blood oxygenation, and/or other physiological parameters. The cuff may vibrate and/or tighten on the extremity of subject 12 to provide information about the cues to subject 12, such as a transition between inhalation and/or exhalation, or that flow should be increased or decreased.

As another non-limiting example of the manner in which user interface 18 may communicate information about the cues to subject 12, user interface 18 may include a display screen that provides subject 12 with text conveying information about the cues.

In one embodiment, interface module 40 controls user interface 18 to provide information about cues that are currently being delivered to subject 12 and/or future cues.

Interface module 40 may also be configured to provide visual focal cues for subject 12 via the user interface 18. The visual focal cues may include different color lights or displays of images, animations, or other visuals. Subject 12 may focus on these visual focal cues during labor. Interface module 40 may also provide relaxing music or other sounds (e.g., sounds associated with nature or other calming sounds) via user interface 18. In some embodiments, interface module 40 may also provide aromatherapy through user interface 18. Alternatively or additionally, interface module 40 may also be configured to provide messages of encouragement via user interface 18. The timing or pattern of these focal cues, music, messages, or aromatherapy may be determined based on information received from imaging subsystem 15, contraction sensor 23, and/or physiological sensors 21.

In some embodiments, interface module 40 may be configured to provide recommended body positions for subject 12 via user interface 18. Changing body positions at an interval (e.g., 30 minutes or any other time periods) between contractions may improve comfort. Information received may be used to determine the timing of the recommendations to change body positions. For example, information received from contraction sensor 23 may be used to determine the time period between contractions when the recommendations should be provided.

Figure 3:
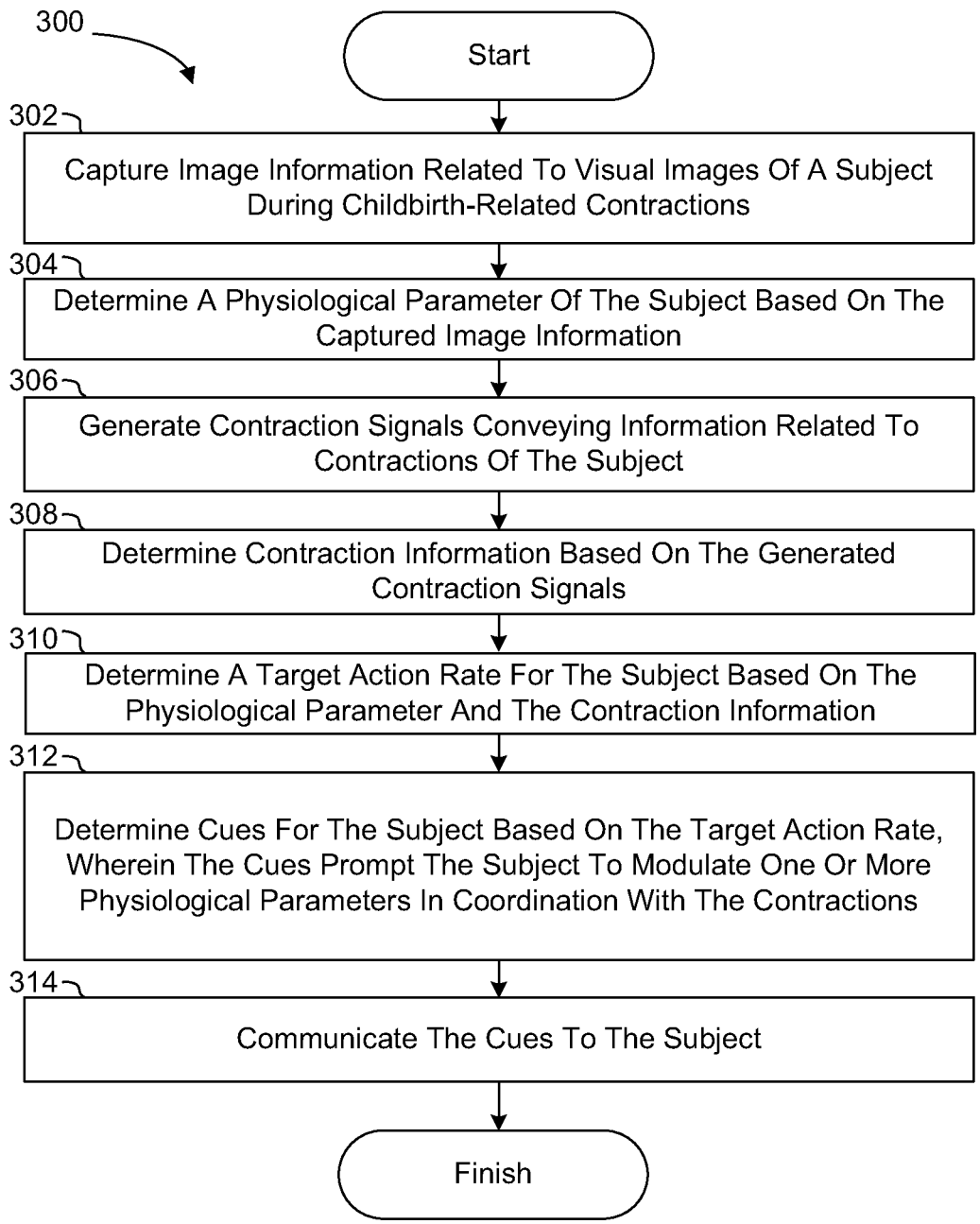
FIG. 3 illustrates a method of prompting a subject to consciously alter one or more physiological parameters during childbirth-related contractions, according to one or more embodiments.

FIG. 3 illustrates a method 300 for prompting a subject to consciously alter one or more physiological parameters during childbirth. The operations of method 300 are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting. In some embodiments, method 300 may be implemented in a system that is similar to or the same as system 10 (shown in FIG. 1 and described above).

At an operation 302, image information is captured related to visual images of a subject during childbirth-related contractions. In one embodiment, step 302 is performed by an imaging subsystem that is the same as or similar to imaging subsystem 15 (shown in FIG. 1 and described above).

At an operation 304, a physiological parameter is determined of the subject based on the captured image information. In one embodiment, step 304 is performed by a parameter determination module that is the same as or similar to parameter determination module 32 (shown in FIG. 1 and described above).

At an operation 306, contraction signals are generated that convey information related to contractions of the subject. In one embodiment, step 306 is performed by a contraction sensor that is the same as or similar to contraction sensor 23 (shown in FIG. 1 and described above).

At an operation 308, contraction information is determined based on the generated contraction signals. In one embodiment, step 308 is performed by a contraction detection module that is the same as or similar to contraction detection module 36 (shown in FIG. 1 and described above).

At an operation 310, a target action rate is determined for the subject based on the determined physiological parameter and the contraction information. In one embodiment, step 310 is performed by a target action module that is the same as or similar to target action module 38 (shown in FIG. 1 and described above).

At an operation 312, cues are determined for the subject based on the target action rate, wherein the cues prompt the subject to modulate one or more physiological parameters in coordination with the contractions. In one embodiment, step 312 is performed by a target action module that is the same as or similar to target action module 38 (shown in FIG. 1 and described above).

At an operation 314, the cues are communicated to the subject. In one embodiment, step 314 is performed by an interface module that is the same as or similar to interface module 40, operating in conjunction with user interface 18 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to prompt a subject to consciously alter one or more physiological parameters during childbirth-related contractions, the system comprising:

an imaging subsystem configured to capture image information related to visual images of the subject during childbirth-related contractions;
a contraction sensor configured to generate contraction signals conveying information related to contractions of the subject;
a user interface; and
one or more hardware processors configured by non-transitory machine-readable instructions to:
determine one or more current breathing parameters and one or more current cardiovascular parameters of the subject based on the captured image information;
determine contraction information based on the generated contraction signals from the contraction sensor;
obtain a target breathing rate and an actual breathing rate of the subject during the contractions;
determine a target action rate based on a difference between the target and actual breathing rates during the contractions, the one or more current breathing parameters, the one or more current cardiovascular parameters, and the contraction information;
determine cues for the subject based on the target action rate, wherein the cues prompt the subject to modulate one or more physiological parameters in coordination with the contractions of the subject; and
communicate the cues to the subject via the user interface.

2. The system of claim 1, wherein the target action rate includes a current target breathing rate for an upcoming contraction, and wherein the determined cues include breathing cues.

3. The system of claim 2, wherein the user interface includes haptic stimulus to communicate the breathing cues to the subject.

4. The system of claim 2, wherein the contraction information includes an onset time, an intensity level, a duration, and a frequency of the contractions of the subject, and wherein the current target breathing rate is further determined based on the onset time, the intensity level, the duration, and the frequency of the contractions of the subject.

5. The system of claim 1, further comprising a breathing detection module configured to determine the target and actual breathing rates of the subject during the contractions.

6. A method for determining and communicating cues to a subject to consciously alter one or more physiological parameters during childbirth-related contractions, the method comprising:

capturing image information related to visual images of the subject during childbirth-related contractions;
determining one or more current breathing parameters and one or more current cardiovascular parameters of the subject based on the captured image information;
generating contraction signals conveying information related to contractions of the subject;
determining contraction information based on the generated contraction signals;
obtaining a target breathing rate and an actual breathing rate of the subject during the contractions;
determining a target action rate for the subject based on a difference between the target and actual breathing rates during the contractions, the one or more current breathing parameters, the one or more current cardiovascular parameters, and the contraction information;
determining cues for the subject based on the target action rate, wherein the cues prompt the subject to modulate one or more physiological parameters in coordination with the contractions of the subject; and communicating the cues to the subject.

7. The method of claim 6, wherein the target action rate includes a current target breathing rate for an upcoming contraction, and wherein the determined cues include breathing cues.

8. The method of claim 7, wherein the breathing cues include haptic stimulus.

9. The method of claim 7, wherein the contraction information includes an onset time, an intensity level, a duration, and a frequency of the contractions of the subject, and wherein the current target breathing rate is further determined based on the onset time, the intensity level, the duration, and the frequency of the contractions of the subject.

10. The method of claim 7, further comprising:
determining the obtained target and actual breathing rates of the subject during the contractions.

11. A system configured for prompting a subject to consciously alter one or more physiological parameters during childbirth-related contractions, the system comprising:

means for capturing image information related to visual images of the subject during childbirth-related contractions;

means for determining one or more current breathing parameters and one or more current cardiovascular parameters of the subject based on the captured image information;

means for generating contraction signals conveying information related to contractions of the subject;

means for determining contraction information based on the generated contraction signals;

means for obtaining a target breathing rate and an actual breathing rate of the subject during the contractions;

means for determining a target action rate for the subject based on a difference between the target and actual breathing rates during the contractions, the one or more current breathing parameters, the one or more current cardiovascular parameters, and the contraction information;

means for determining cues for the subject based on the target action rate, wherein the cues prompt the subject to modulate one or more physiological parameters in coordination with the contractions of the subject; and means for communicating the cues to the subject.

12. The system of claim 11, wherein the target action rate includes a current target breathing rate for an upcoming contraction, and wherein the determined cues include breathing cues.

13. The system of claim 12, wherein the breathing cues include haptic stimulus.

14. The system of claim 12, wherein the contraction information includes an onset time, an intensity level, a duration, and a frequency of the contractions of the subject, and wherein the current target breathing rate is further determined based on the onset time, the intensity level, the duration, and the frequency of the contractions of the subject.

15. The system of claim 12,
wherein the means for obtaining the target and actual breathing rates of the subject during the contractions determines the target and actual breathing rates of the subject during the contractions.

* * * * *